United States Patent [19]

Wilkins et al.

[11] 4,029,470

[45] June 14, 1977

[54] AUTOMATED SINGLE-SLIDE STAINING DEVICE

[75] Inventors: Judd R. Wilkins; Stacey M. Mills, both of Hampton, Va.

[73] Assignee: The United States of America as represented by the Administrator of the National Aeronautics and Space Administration, Washington, D.C.

[22] Filed: Oct. 29, 1975

[21] Appl. No.: 626,942

[52] U.S. Cl. .................................. 8/94.11; 8/3; 23/253 A; 23/259; 23/292; 118/6; 118/7; 118/9; 118/313; 424/3; 427/4

[51] Int. Cl.² .................................... D06P 3/00

[58] Field of Search ................ 8/3, 94.11; 118/6, 7, 118/9, 313; 424/3; 427/4; 23/253 A, 259, 292

[56] References Cited
UNITED STATES PATENTS 3,352,280  11/1967  Hughes et al. .................... 118/9
3,667,896  6/1972  McCormick et al. ................ 8/3
3,691,988  9/1972  Clarke ............................. 118/6
3,837,795  9/1974  Becker et al. ..................... 8/3

*Primary Examiner*—John Kight, III
*Attorney, Agent, or Firm*—Howard J. Osborn; Wallace J. Nelson; John R. Manning

[57] ABSTRACT

A simple apparatus and method is disclosed for making individual single Gram stains on bacteria inoculated slides to assist in classifying bacteria in the laboratory as Gram-positive or Gram-negative. The apparatus involves positioning a single inoculated slide in a stationary position and thereafter automatically and sequentially flooding the slide with increments of a primary stain, a mordant, a decolorizer, a counterstain and a wash solution in a sequential manner without the individual lab technician touching the slide and with minimum danger of contamination thereof from other slides.

18 Claims, 3 Drawing Figures

AUTOMATED SINGLE-SLIDE STAINING DEVICE

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

One of the most frequently performed operations in a microbiology laboratory is a staining procedure, the Gram stain, which is used to broadly classify bacteria as either Gram-positive or Gram-negative. The Gram stain, normally, is a manual four-step operation in which a primary stain is applied to a bacterial smear on a slide, followed by a mordant, usually an iodine solution, a decolorizer and a counterstain. It would be highly desirable to automate this procedure in order to free the operator or lab technician for other work and to remove certain subjective evaluations such as the time required for colorization. Two known automated Gram stain machines have been developed and both units operate on a "batch" system where slides are automatically transported through troughs containing staining solutions. The obvious drawback to these prior art systems is the possibility of contamination, either through the staining solution themselves or by transfer from previously processed slides. This uncertainty as to the possible contamination has precluded wide acceptance of the batch system by most laboratories.

It is therefore an object of the present invention to provide a novel apparatus for automatically making individual single laboratory Gram-stains on bacteria-inoculated slides.

Another object of the present invention is an apparatus for making individual laboratory Gram-stains that minimize human error as well as the possibility of contamination of the individual slides.

A further object of the present invention is an apparatus for automatically flooding an inoculated slide with increments of a primary stain, a mordant, a decolorizer, a counterstain and a wash solution in a sequential manner.

An additional object of the present invention is a method of making individual Gram stains in an automatic and sequential operation without extended handling by the lab technician.

SUMMARY OF THE INVENTION

The foregoing and other objects of the present invention are attained by providing a plurality of individual liquid reservoirs containing a primary stain, a mordant, a decolorizer, a counterstain and a wash solution connected to an automated system whereby the liquids from the reservoirs are automatically released to flood a bacteria-inoculated slide in a sequential timed manner. The apparatus for performing this procedure includes a vertically disposed support plate having a front and a back surface with brackets attached to the front surface of the support plate to retain conduits leading from a plurality of liquid reservoirs containing the liquids and terminating at an essentially common exit area and this exit area being disposed adjacent a support mechanism for a bacteria-inoculated slide. In the preferred embodiment the slide support mechanism comprises a bracket extending horizontally from the vertical plate and a ring element connected to the bracket for receiving a funnel therein with the slide resting on and spanning across the open face of the funnel. The funnel exit is connected to a waste discharge tube in such manner that when the stain liquid components flood the inoculated slide the waste material flows into the funnel and out the waste discharge tube to a suitable disposal area.

BRIEF DESCRIPTION OF THE DRAWINGS

A more complete appreciation of the present invention and many of the attendant advantages thereof will be more readily apparent as the same becomes better understood with reference to the following detailed description when considered in connection with the accompanying drawings wherein.

Figure 1:
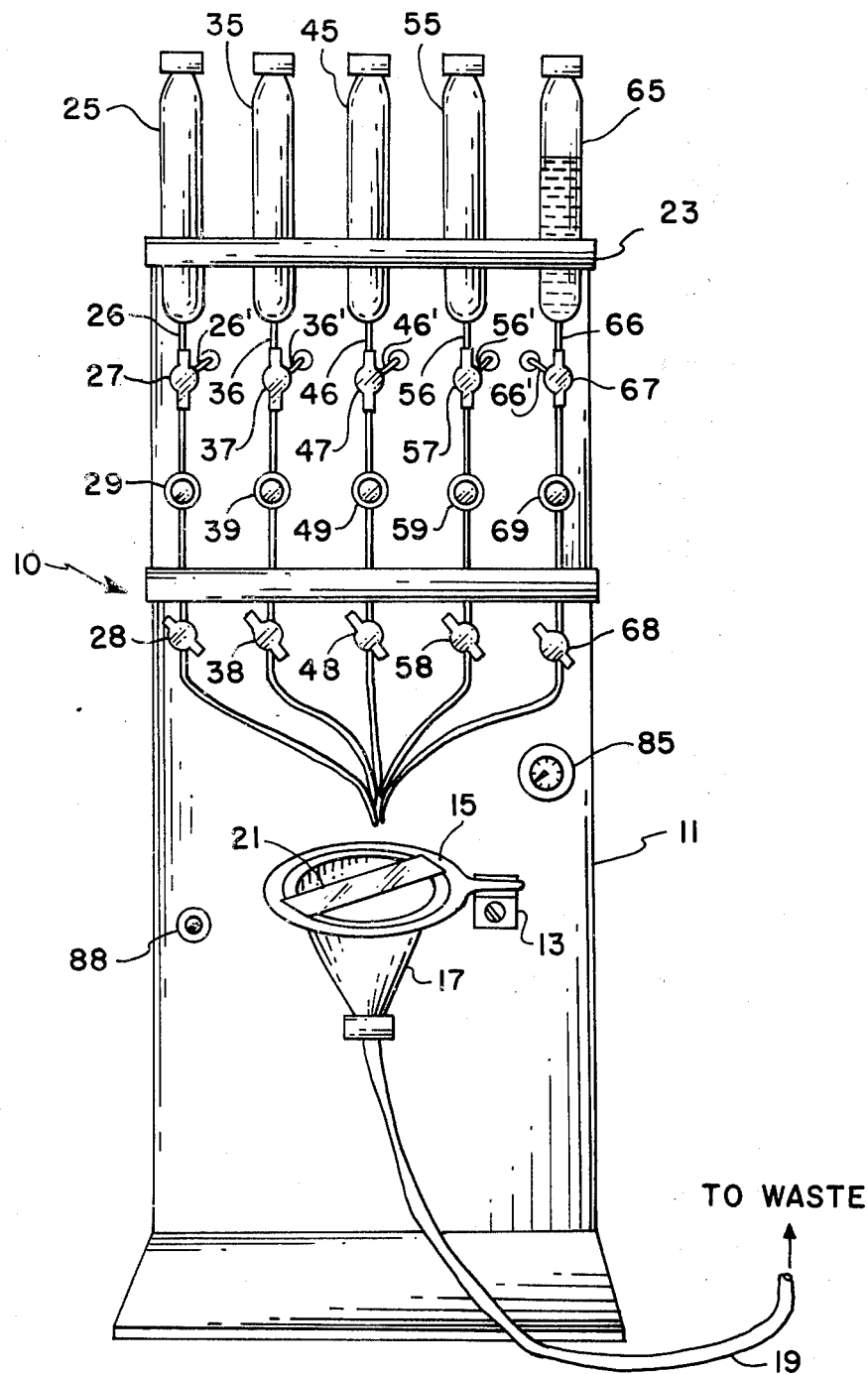
FIG. 1 is a front view of the apparatus employed in making the individual Gram stains according to the present invention.
Figure 2:
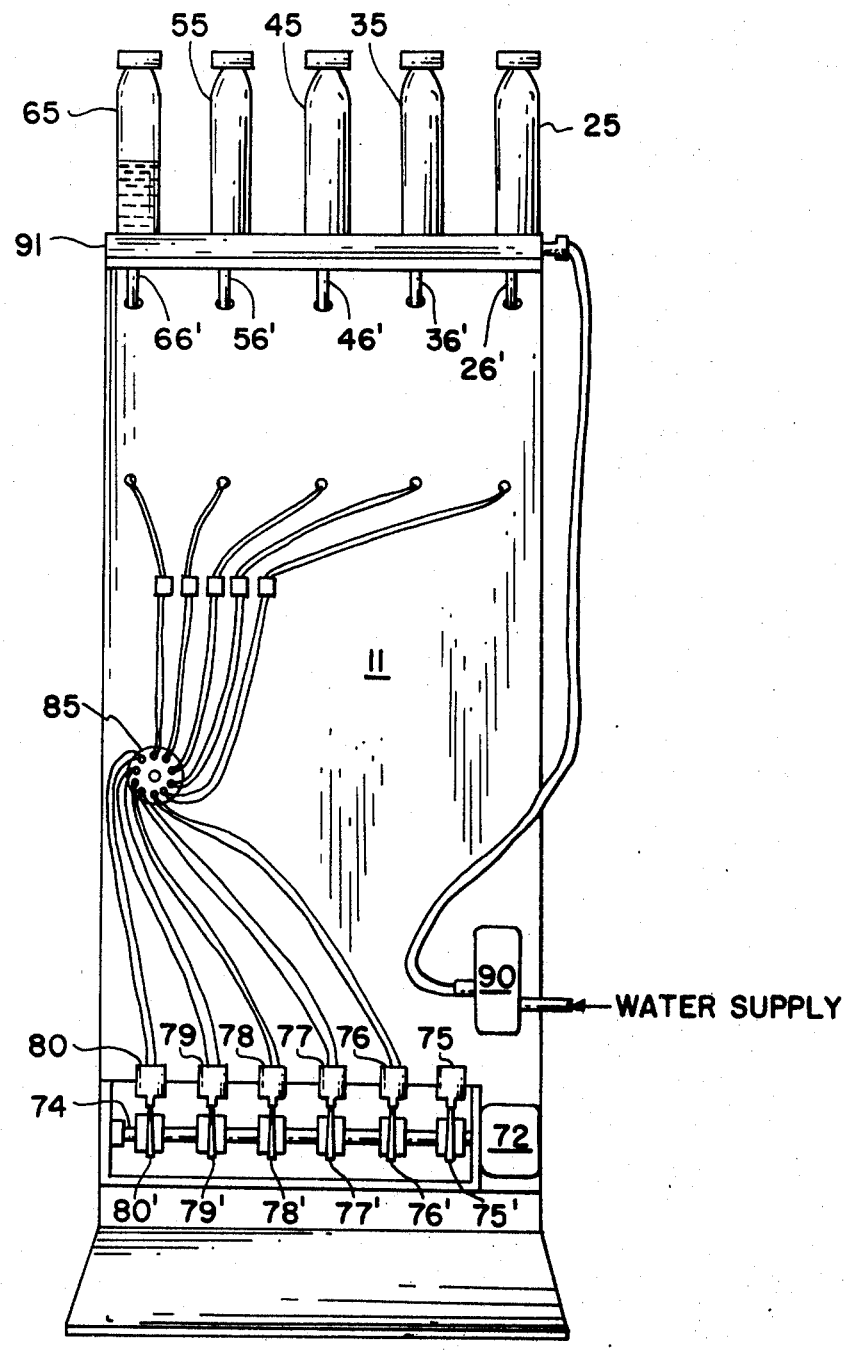
FIG. 2 is a back view of the apparatus of FIG. 1 with parts being schematically shown.

Referring now to the drawings more particularly to FIGS. 1 and 2, the apparatus for making automatic single Gram-stains according to the present invention is generally designated by reference numeral 10. Apparatus 10 includes a vertically disposed support plate 11 having a first bracket 13 attached to the front surface thereof. A ring element 15 is connected to and extends from bracket 13 in a horizontal relationship relative to vertical disposed support plate 11. Ring element 15 serves to receive a funnel, such for example, glass funnel 17 which terminates with a waste discharge tube 19 at the small opening thereof. The diameter of ring element 15 and the contained funnel 17 are such that permits the positioning of a bacteria inoculated slide 21, a conventional type glass slide used in microscopic studies, to rest on the open surface of funnel 17 with the slide 21 spanning the funnel diameter. A second bracket 23 is attached to vertical disposed plate 11 in a spaced relationship from first bracket 13. Second bracket 23 is provided with a plurality of openings therein for receiving, respectively, liquid reservoirs 25, 35, 45, 55 and 65. Each of these reservoirs is of the same basic construction and includes a conduit leading therefrom and terminating in an open tip portion at an essentially common area adjacent the slide 21 in such position that the liquid emanating from each tip portion will flood the inoculated slide. The conduits for reservoirs 25, 35, 45, 55 and 65 are designated, respectively, by reference numerals 26, 36, 46, 56, and 66. Each of these conduits is provided with a manually operable stopcock (two-way) designated, respectively, by reference numerals 27, 37, 47, 57 and 67 and a second manually operable stopcock disposed along the respective conduits and spaced from the first stopcock and designated, respectively, as reference numerals 28, 38, 48, 58 and 68.

These stopcocks are designed to permit adjustment of the rate of liquid flow to slide 21. In addition, two-way stopcocks 27, 37, 47, 57 and 67 serve to alternately connect the system with reservoirs 25, 35, 45, 55 and 65 and a water manifold 91 (FIG. 2). When the stopcocks are turned to connect with manifold 91 conduits 26, 36, 46, 56 and 66 are closed off and branch conduits 26', 36', 46', 56' and 66' are opened. This permits flushing of the system with water to remove excess stains from the conduits and stopcocks as will be further explained hereinafter. A solenoid valve is provided in each conduit and disposed intermediate each of the first and second stopcocks and designated, respectively, by reference numerals 29, 39, 49, 59 and 69.

Referring now more particularly to FIG. 2, the electrically actuated motor, schematically shown at 72, serves to drive a shaft 74 having a plurality of cam surfaces designated, respectively, by reference numeral 75', 76', 77', 78', 79' and 80'. These cam surfaces serve to sequentially close microswitches designated, respectively, by reference numerals 75, 76, 77, 78, 79 and 80. Microswitch 75, when closed, serves to complete the electric circuit to motor 72 as will be further explained hereinafter. Microswitches 76, 77, 78, 79 and 80, when closed, serve to actuate the respective solenoid valves 29, 39, 49, 59, and 69.

Figure 3:
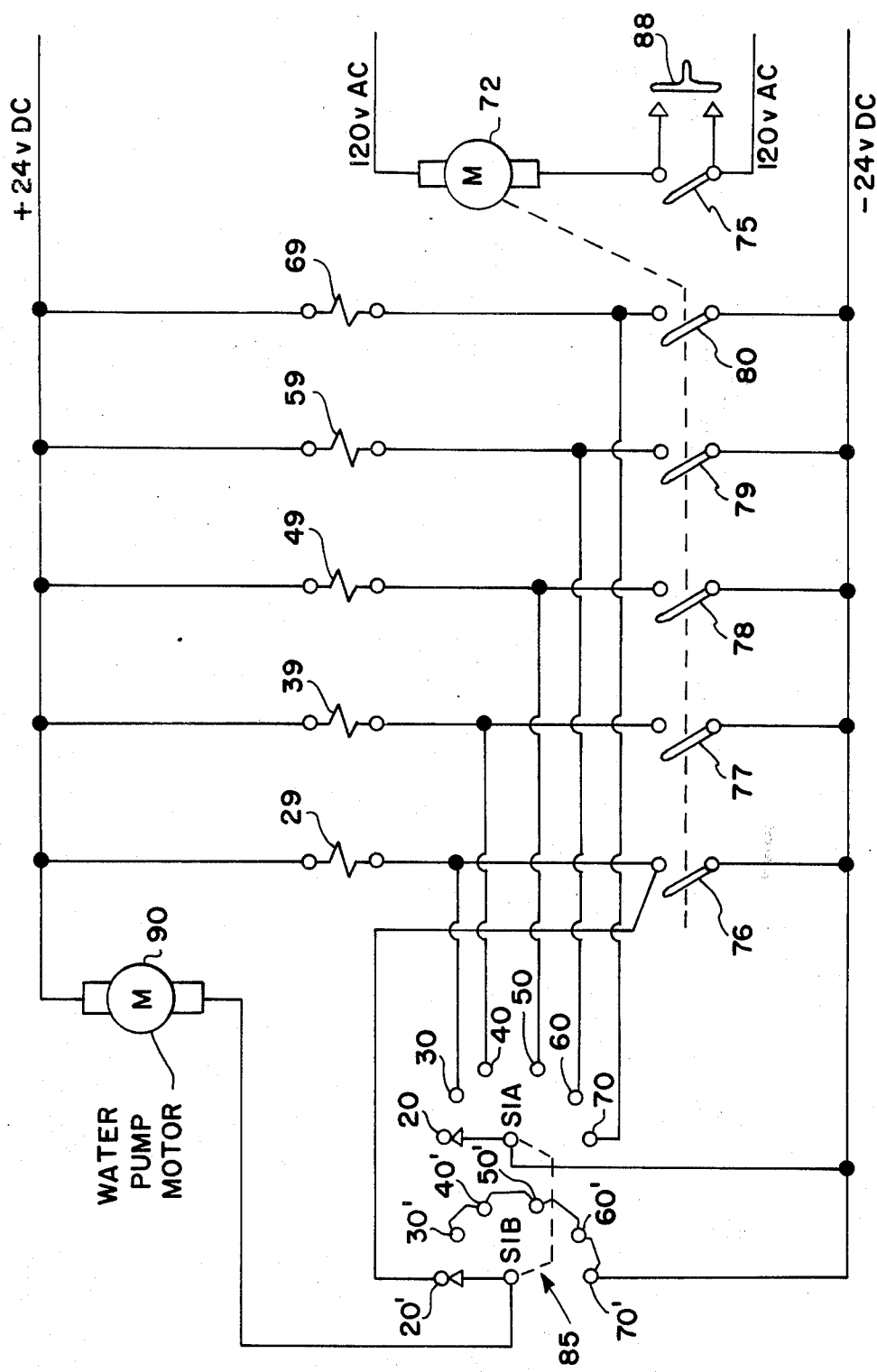
FIG. 3 is a schematic circuit diagram illustrating the electrical operation of the present invention.

As shown more particuarly in FIG. 3, a six-position selector switch may also be employed for manually operating as well as for flushing the entire system. In this event, selector switch 85 (FIG. 1) may be manually operated to actuate each of solenoid valves 29, 39, 49, 59 and 69, separately as will be further explained hereinafter.

OPERATION

The operation of the present invention is now believed apparent. After inoculating a slide 21 with bacteria, it is positioned on funnel 17. Liquid reservoirs 25, 35, 45, 55 and 65 are filled, respectively, with primary stain, for example, gentian violet, Gram's iodine solution, decolorizer consisting of two parts 95% ethyl alcohol and one part acetone, 1 percent aqueous safranin and distilled water for the rinse cycles. The first and second stopcocks located in each conduit leading from the reserviors are manually operated to control the flow rate of the stains and reagents employed in the Gram stain operation. The start button for motor 72 is located on the front surface of vertically disposed plate 11 and designated by reference numeral 88. A complete staining cycle is initiated by holding start button 88 in position for 30 seconds. This permits drive shaft 74 to start rotation and cause the first of six cams located thereon and designated by reference numeral 75' to close mircoswitch 75. Cam 75' is designed to maintain microswitch 75 closed until the end of the automated operation at which time the cam permits the microswitch to open the circuit and stop motor 72. The remaining microswitches 76, 77, 78, 79 and 80 are each closed by their respective cams 76', 77', 78', 79' and 80' in automated fashion as shaft 74 rotates. The individual cam faces are adjustable about shaft 74 in a conventional manner by suitable setscrews or the like to permit any combination of time intervals required in a particular staining process. Cam 80', serving to close microswitch 80 that actuates solenoid 69 for the rinse cycle, is provided with one fixed and three adjustable cam surfaces to permit actuation of the rinse cycle after each stain or reagent addition. Thus, in a specific operation when drive shaft 74 starts rotation, microswitch 75 is closed by cam 75', microswitch 76 is closed by cam 76' for a predetermined time interval during which time solenoid 29 permits release of the primary stain from reservoir 25 and as cam 76' permits microswitch 76 to open, cam 80' closes microswitch 80 to actuate solenoid 69 and flood slide 21 with rinse water from reservoir 65. Shaft 74 continues to rotate and sequentially actuates each of microswitches 77, 78 and 79 through their respective cams 77', 78' and 79'. Microswitch 80 is actuated by its cam 80' each time as any of these microswitches (76, 77, 78 and 79) is opened. After the final rinse cycle, cam 75' has rotated to a position to open the circuit and stop motor 72. As mentioned hereinbefore the system is also adapted to permit manual staining as well as flushing of the entire system with water to remove excess stain from the various conduits and stopcocks.

In this event, as the switch knob (FIG. 1) is rotated the switch contacts of portions of S1A and S1B are simulataneously moved from the "off" position as designated respectfully by reference numerals 20 and 20' to contact points 30 and 30'. In this position solenoid 29 is actuated to release the stain contained in reservoir 25 and water pump motor 90 serves to pump water from a suitable source, such for example tap water, to manifold 91 (FIG. 2). Inasmuch as two-way stopcocks 27, 37, 47, 57 and 67 (FIG. 1) are turned in such position as to open conduits 26, 36, 46, 56, and 66, no water flows from manifold 91. As soon as manifold 91 is filled with water, pump motor 90 is designed to cease the pumping action while continuing to run. As the water in manifold 91 is depleted, pump motor 90 replenishes the supply. The time for flooding the slide 21 with the primary stain is measured by a stopwatch and will usually be 1 minute or less. Switch 85 is then rotated to make contact at points 70 and 70' for rinsing of slide 21 with water from reservoir 69. After the desired rinsing time interval, switch 85 is manually rotated to contacts 40 and 40' for flooding slide 21 with the mordant. One suitable mordant solution frequently used for this purpose consists of a solution of 1 gram of iodine and 2 grams of potassium iodide in 300 milliteters of distilled water. After flooding slide 21 with this mordant for 1 minute, or less, the slide is again rinsed by rotating the switch contacts to points 70 and 70' as before. This manual rotation is repeated for contacts 50 and 50' and 60 and 60' for treating the inoculted slide 21 with the decolorizer solution and counterstain, respectively, from reservoirs 45 and 55 with the rinse cycle being employed after each operation, as before. Some laboratory workers prefer to blot Gram slides dry after each rinse cycle and before applying the next stain or reagent. The time for completng a Gram stain cycle by either the automated or manual operation of the present invention may be varied as desired by the operator. In one specific Gram stain cycle, a total of 4.8 minutes were utilized and the times required for each stage of the staining process were as follows:

| STAGE | TIMES, MINUTES |
|---|---|
| Gentian Violet | |
|    Stain Dispersion | 0.25 |
|    Total Stain Time | 1.00 |
| Rinse Cycle | 0.40 |
| Iodine | |
|    Stain Dispersion | 0.15 |
|    Total Stain Time | 0.40 |
| Rinse Cycle | 0.40 |
| Decolorizer | 0.10 |
| Rinse Cycle | 0.40 |
| Safranin | |
|    Stain Dispersion | 0.40 |
|    Total Stain Time | 0.90 |
| Rinse Cycle | 0.40 |
| Total | 4.80 |

The cultures employed to illustrate the present invention were obtained from the American Type Culture Collection of Rockville, Md. and included *Pseudomonas aeruginosa*, 19429; *Proteus mirabilis*, 12453; *Citrobacter intermedium*, 6750; *Escherichia coli*, 12014; *Enterobacter aerogenes*, 13882; *Streptococcus faecalis*, 12755; *Streptococcus pyogenes*, 12384; *Staphylococcus epidermidis*, 155; *Sarcina lutea*, 381 and *Staphylococcus aureus*, 12600. The cultures were maintained on Trypticase soy agar (TSA, BBL) slants at 5° C. and all smears for staining were prepared from 24 hr cultures grown in Trypticase soy broth (TSB, BBL). Smears of the cultures were prepared and heat fixed according to standard methods and each culture was Gram stained by the automatic system of the present invention and by conventional manual techniques. Stain exposure times were the same for both procedures. In addition, ten smears were prepared, each consisting of a mixture of a Gram-positive with a Gram-negtive organism, and these smears were also stained by the present automated system and by conventional manual methods.

All stains employed in the present specific example were purchased from the Fischer Scientific Company of Fair Lawn, N.J. The liquid reservoirs containing the various stains were glass containers coated on the outside with black enamel paint to prevent stain deterioration by light. The water reservoir was a plain glass container and was not provided with the enamel coating. The five solenoid valves were model number B2DA102B, obtained from the Skinner Electric Valve Company of New Britian, Conn. These solenoid valves were controlled by a timing motor purchased from Minarik Electric Company, Los Angeles, Calif., model no. 11C-NSY. The gentian violet employed in reservoir 25 was Weigert No. 1 and the mordant in reservoir 26 was Gram's iodine solution. The decolorizer used was a solution of two parts 95% ethyl alcohol and one part acetone and the counterstain was a safranin solution composed of 10 ml of a 2.5% solution in 95% ethanol and added to 100 ml of distilled water.

It is thus seen that the present invention describes an automated Gram staining device based on the single slide principle which has all the features of automation without the possibility of contamination that is characteristic of batch-staining systems. The present invention is also flexible enough to accommodate other types of staining procedures used in microbiology laboratories other than the Gram stain as will be readily apparent to those skilled in the art.

Although no attempt was made to quantitatively grade the stained preparation, subjective evaluations by different observers indicated no difference in the quality of the smears stained by the automatic system of the present invention versus the manual method normally employed.

These evaluations applied equally well to both single and mixed cultures. Although the time required to complete a staining cycle by the automatic method was considerably longer than the manual procedure, normally employed, this time could be reduced markedly by eliminating the long delays between each step of the automatic procedure. In addition, no adverse effects were observed either in the mechanical operation of the automatic machinery described herein, or quality of stains, when the procedures were conducted on different days over a period of 30 days.

As in the case of batch techniques employed in the prior art, the major advantages of the automatic stain procedure described in the present invention consists of first, freeing the operator for other work in the laboratory and second, elimination of any subjective evaluation as to length of staining or decolorizing time. Such a procedure assures uniform and repeatable staining of smears, free of any operator involvement. On the other hand, in contrast to batch methods, the present invention reduces the possibility of cross contamination from other slides. This invention would be useful in any laboratory where the Gram stain is performed and should be especially useful to the practicing clinician who requires a rapid and easily obtainable Gram stain specimen in order to aid in diagnosis of suspected infections.

Although the invention has been described relative to a specific embodiment thereof, there are obviously many modifications and variations of the invention that will be readily apparent to those skilled in the art in the light of the above teachings. For example, the various liquid reservoirs containing the stains need not be attached directly to the support for positioning the inoculated slide, but could be provided at a permanent location with the slide support being moved to this location when an automatic stain is desired. Other stains and reagents that are conventionally employed in making Gram stains may also obviously be substituted for the specific examples disclosed herein without departing from the spirit or scope of the invention. The entire system may be readily adapted to operate on 120v a.c. and avoid the necessity of the 24v d.c. power supply. Also, specific details in the slide support mechanism, the waste discharge system, and the like, described herein are to be considered exemplary only and are merely to illustrate the invention with no intention of limiting the invention to these specific details. These, and other modifications and variations, are considered possible in the light of the above teachings and will be readily apparent to those skilled in the art.

It is therefore to be understood that the invention may be practiced otherwise than as specially described herein.

What is claimed as new and desired to be secured by Letters Patent of the United States is:

1. Apparatus for making laboratory Gram stains of Gram-positive and Gram-negative bacteria on individual inoculated slides comprising:
    an inoculated laboratory slide and support means for receiving and supporting the slide,
    a plurality of liquid dispersing means each having a discharge outlet constructed and arranged to flood said inoculated slide with liquid,
    waste collector and discharge means extending from said support means for receiving the liquid from said plurality of liquid dispersing means when said slide is flooded thereby,
    individual valve means for each of said plurality of liquid dispersing means,
    individual actuator means for selectively opening and closing each of said valve means,
    timing means connected to and, when initiated, serving to sequentially actuate said individual actuator means to sequentially open and close each of said valve means in a predetermined sequence to flood said inoculated slide with increments of a primary stain, a mordant, a decolorizer, a counterstain and a wash solution, and
    means for initiating said timing means.

2. The apparatus of claim 1 including a vertically disposed support plate, a ring element extending horizontally from said vertically disposed support plate, said waste collector and discharge means comprising a funnel having a discharge tube attached thereto, said funnel being received and supported by said ring element and said inoculated slide being positioned to span the open face of said funnel for support thereby.

3. The apparatus of claim 1 including a vertically disposed support plate,
a bracket attached to said support plate,
said plurality of liquid dispersing means including a plurality of liquid reservoirs supported by said bracket,
a conduit extending from each of said plurality of liquid reservoirs,
each said conduit having a first and a second manually operable stopcock disposd in spaced relationship along the length thereof,
each said conduit terminating in an open tip portion, and
said tip portions serving as the discharge outlets for said liquid dispersing means.

4. The apparatus of claim 3 wherein said individual valve means comprises a solenoid valve disposed in each said conduit, each said solenoid valve being disposed intermediate each of said first and said second manually operated stopcocks and in electrical connection with a power supply.

5. The apparatus of claim 4 wherein said individual actuator means comprises a plurality of microswitches equal in number to and in electrical connection with said solenoid valves, an electrically operated timing motor serving as said timing means, said timing motor serving to drive a shaft having a plurality of cam surfaces thereon, and said cam surfaces being constructed and arranged to sequentially actuate said microswitches.

6. The apparatus of claim 4 wherein said individual actuator means comprises a six-position ganged selector switch, said ganged selector switch being manually operated to selectively actuate each of said solenoid valves.

7. The apparatus of claim 5 including means for flushing said apparatus with water to remove excess stain and reagents from the components thereof after a staining operation cycle.

8. The apparatus of claim 7 wherein said means for flushing said apparatus with water includes a first segment of said selector switch serving to close a separate electric circuit and a water pump attached to said support plate and actuated by said closing of said first segment of said selector switch to initiate pumping of water for flushing of said apparatus.

9. The apparatus of claim 8 wherein said water pump is connected to a water supply and including a water storage manifold for receiving water pumped by said pump from said water supply.

10. The apparatus of claim 9 wherein said manifold is attached to said support plate on the surface thereof opposite to said plurality of liquid reservoirs and including a branch conduit leading from said manifold through said support plate to each of said first stopcocks disposed in said conduits extending from each of said plurality of liquid reservoirs, each of said first stopcocks being two-way stopcocks and manually movable from a closed position to a first position connecting said branch conduits leading from said manifold and a second postion connecting said conduits leading from said plurality of reservoirs to the conduit discharge channel, a second segment of said selector switch including individual contacts for initiating each of said solenoids and permit water from said manifold to flush the individual components of the system as each solenoid valve is opened.

11. Apparatus for automatically making single laboratory Gram stains on bacteria inoculated slides to assist in classifying bacteria as Gram-positive or Gram-negative, comprising:
a vertically disposed support plate having a front and a back surface,
a first bracket attached to said front surface of said support plate,
slide support means retained by said first bracket and serving to support an inoculated slide,
waste collector and discharge means extending from said slide support means,
a second bracket attached to said front surface and spaced from said first bracket,
a plurality of liquid reservoirs supported by said second bracket,
a liquid conduit leading from each of said liquid reservoirs and each terminating in an open tip portion at an essentially common area adjacent said slide support means,
each said conduit having a first and a second manually operable stopcock disposed in spaced relationship along the length thereof,
a solenoid valve in each said conduit and disposed intermediate each said first and said second stopcocks,
a timing motor positioned on the back surface of said support plate,
a plurality of cams attached to a shaft driven by said timing motor,
a plurality of microswitches equal in number to said cams and activated individually thereby,
said mircoswitches, save one, each serving to activate one of said solenoid valves to cause discharge of liquid from the respective reservoirs in a controlled operation so as to automatically flood the slide with increments of a primary stain, a mordant, a decolorizer, a counterstain and a wash solution in a sequential manner.

12. The apparatus of claim 11 wherein the cam actuating said one microswitch is constructed and arranged to close said one microswitch prior to closing of the other microswitches and to maintain said microswitch closed to keep said timing motor is a closed electric circuit until the staining procedure is complete and thereafter said one microswitch is released by said cam to open the electric circuit to said timing motor.

13. The apparatus of claim 11 including a ring element connected to said first bracket and extending horizontally from said vertically disposed support plate, said waste collector and discharge means comprising a funnel having a discharge tube attached thereto, said funnel being received and supported by said ring element and said inoculated slide being positioned to span the open face of said funnel for support thereby.

14. A method of making laboratory Gram stains of Gram-positive and Gram-negative bacteria on individual inoculated slides comprising:
inoculating a laboratory slide with bacteria,
fixedly positioning the inoculated slide over a waste collector, providing a plurality of liquid dispersing containers each individually housing a primary stain, a mordant, a decolorizer and a wash solution and each having a discharge outlet constructed and arranged to flood said inoculated slide, automatically flooding the inoculated slide with sequentially timed increments of a primary stain, a mordant, a decolorizer, a counterstain and a wash solution, and recovering a Gram stain slide.

15. The method of claim 14 including the step of collecting the liquids from the flooded slide and conveying same to a waste area.

16. The method of claim 14 including the steps of flooding the inoculated slide with the wash solution after each of the primary stain, mordant, decolorizer, and counterstain flooding steps.

17. The method of claim 14 wherein the automatic flooding of the inoculated slide by the primary stain, mordant, decolorizer, counterstain and wash solution is controlled by an electrically driven motor.

18. The method of claim 14 wherein the automatic flooding of the inoculated slide by the primary stain, mordant, decolorizer, counterstain and wash solution is manually controlled.

* * * * *